United States Patent [19]
Montagnier et al.

[11] Patent Number: 5,889,158
[45] Date of Patent: *Mar. 30, 1999

[54] METHODS AND KITS FOR THE DETECTION OF HUMAN IMMUNODEFICIENCY VIRUS TYPE 2 EMPLOYING HIV-2 SPECIFIC ANTIBODIES AND ANTIGENS

[75] Inventors: Luc Montagnier, Le Plessis; Denise Guetard, Paris; Francoise Brun-Vezinet, Paris; Francois Clavel, Paris, all of France

[73] Assignee: Institut Pasteur, Paris, France

[*] Notice: The term of this patent shall not extend beyond the expiration date of Pat. No. 5,030,718.

[21] Appl. No.: 466,704

[22] Filed: Jun. 6, 1995

Related U.S. Application Data

[60] Continuation of Ser. No. 202,260, Feb. 25, 1994, Pat. No. 5,597,896, which is a division of Ser. No. 929,432, Aug. 14, 1992, Pat. No. 5,364,933, which is a division of Ser. No. 911,364, Jul. 13, 1992, abandoned, which is a continuation of Ser. No. 771,893, Oct. 7, 1991, abandoned, which is a continuation of Ser. No. 365,117, Jun. 12, 1989, abandoned, which is a division of Ser. No. 835,228, Mar. 3, 1986, Pat. No. 4,839,288.

[30] Foreign Application Priority Data

| Jan. 22, 1986 | [FR] | France | 86 00910 |
| Jan. 22, 1986 | [FR] | France | 86 00911 |
| Feb. 6, 1986 | [FR] | France | 86 01635 |
| Feb. 13, 1986 | [FR] | France | 86 01985 |

[51] Int. Cl.$^6$ ............................................. C07K 16/00
[52] U.S. Cl. ..................... 530/387.1; 530/388.3; 530/389.1; 530/389.4; 530/391.3; 435/5; 435/7.9
[58] Field of Search .................. 435/5, 7.9; 530/387.1, 530/388.1, 389.4, 388.3, 389.1, 391.1; 424/188.1, 208.1

[56] References Cited

U.S. PATENT DOCUMENTS

| 4,708,818 | 11/1987 | Montagnier et al. | 435/5 |
| 4,839,288 | 6/1989 | Montagnier et al. | 435/235.1 |
| 5,030,718 | 7/1991 | Montagnier et al. | 530/388.35 |

(List continued on next page.)

FOREIGN PATENT DOCUMENTS

| WO 84/04327 | 11/1984 | WIPO . |
| WO 85/04897 | 11/1985 | WIPO . |
| WO 86/01834 | 3/1986 | WIPO . |

(List continued on next page.)

OTHER PUBLICATIONS

Gallo et al., 1988, Nature (London) 333:564.
Levy, 1993, Microbiol. Rev. 57:183–187, 211–213.
Los Alamos Database, 1990, in Human Retroviruses and AIDS, Myers et al., eds., Los Alamos National Laboratory, New Mexico, pp. IA1–IA3.
Norrby et al., 1988, "Type–specific site–directed human immunodeficiency virus serology", in Vaccines 88, Cold Spring Harbor Laboratory, pp. 335–339.
Strongin, W., 1992, "Sensitivity, specificity, and predictive value of diagnostic tests: definitions and clinical applications", in Laboratory Diagnosis of Viral Infections, Lennette, ed., Marcel Dekker, Inc. New York, pp. 221–219.
Tedder et al., 1988, The Lancet, 2:927–931.
Hunt et al., 1990, AIDS Res. Human Retro. 6:883–898.
Barin et al., "Serological Evidence For Virus Related To Simian T–Lymphotropic Retrovirus III In Residents Of West Africa," *The Lancent,* 1387–1389 (Dec. 21/28, 1985).
Kanki et al., "Serologic Identification and Characterization of a Macaque T–Lymphotropic Retrovirus Closely Related to HTLV–III," *Science,* 228, 1199–1201 (1985).
Clavel et al., "Virology.—LAV type II: A Second Retrovirus Associated with AIDS in West–Africa," *C. R. Acad. Sc. Paris,* 302, 485–488 (1986).
Kestler et al., "Comparison of Simian Immunodeficiency Virus Isolates," *Nature,* 331, 619–622 (1988).
Essex et al., "Essex and Kanki Reply," *Nature,* 331, 621–622 (1988).
Marx, "Probing the AIDS Virus and Its Relatives," *Science,* 236, 1523–1524 (1987).
Daniel et al., "Isolation of T–Cell Tropic HTLV–III–Like Retrovirus from Macaques," *Science,* 228, 1201–1204 (1985).
Fultz et al., "Isolation of a T–lymphotropic Retrovirus from Naturally Infected Sooty Mangabey Monkeys (*Cercocebus atys*)", *Proc. Natl. Acad. Sci., USA,* 83, 5286–5290 (1986).
Clavel et al., "Isolation of a New Human Retrovirus from West African Patients with AIDS," *Science,* 233, 343–346 (1986).
Kanki et al., "New Human T–Lymphotropic Retrovirus Related to Simian T–Lymphotropic Virus Type III," *Science,* 232, 238–243 (1986).
Clavel et al., "Molecular Cloning And Polymorphism Of The Human Immune Deficiency Virus Type 2," *Nature,* 324, 691–695 (1986).

*Primary Examiner*—Laurie Scheiner
*Assistant Examiner*—Jeffrey S. Parkin
*Attorney, Agent, or Firm*—Finnegan, Henderson, Farabow, Garrett & Dunner, L.L.P.

[57] ABSTRACT

This invention discloses the identification and characterization of a novel human retrovirus, originally designated lymphadenopathy-associated virus type II, or LAV-II, and subsequently redesignated the human immunodeficiency virus type 2, or HIV-2. This virus was isolated from West African AIDS patients and propagated on immortalized lymphocytic cell lines or donor peripheral blood mononuclear cells (PBMCs). Immunological and nucleic acid hybridization studies demonstrated that HIV-2 differs significantly from HIV-1, the aetiological agent of AIDS. Additional biochemical characterization identified viral antigens having molecular weights of 16, 26, 36, and 130–140 kDa, as determined by SDS-PAGE. These proteins were subsequently designated p16, p26, gp36, and gp130–140, respectively. These antigens can be employed, inter alia, in the generation of both polyclonal and monoclonal antibodies, which should prove useful in diagnostic and viral antigen purification applications.

7 Claims, 1 Drawing Sheet

U.S. PATENT DOCUMENTS

| | | | |
|---|---|---|---|
| 5,055,391 | 10/1991 | Montagnier et al. | 435/5 |
| 5,135,864 | 8/1992 | Montagnier et al. | 435/235.1 |
| 5,256,561 | 10/1993 | Chin | 435/339.1 |
| 5,304,466 | 4/1994 | DeLeys et al. | 435/5 |
| 5,670,309 | 9/1997 | Norrby et al. | 435/5 |

OTHER PUBLICATIONS

| | | |
|---|---|---|
| WO 86/02382 | 4/1986 | WIPO. |
| WO 86/02930 | 5/1986 | WIPO. |
| WO 86/04423 | 7/1986 | WIPO. |
| WO 87/02892 | 5/1987 | WIPO. |

METHODS AND KITS FOR THE DETECTION OF HUMAN IMMUNODEFICIENCY VIRUS TYPE 2 EMPLOYING HIV-2 SPECIFIC ANTIBODIES AND ANTIGENS

This is a continuation of application Ser. No. 08/202,260, filed Feb. 25, 1994, now U.S. Pat. No. 5,597,896, which is a division of application Ser. No. 07/929,432, filed Aug. 14, 1992, now U.S. Pat. No. 5,364,933, which is a divisional of application Ser. No. 07/911,364, filed Jul. 13, 1992 (now abandoned), which is a continuation application of Ser. No. 07/771,893, filed Oct. 7, 1991 (now abandoned), which is a continuation application of Ser. No. 07/365,117, filed Jun. 12, 1989, now abandoned, which is a division of application Ser. No. 06/835,228, filed Mar. 3, 1986, now U.S. Pat. No. 4,839,288.

The invention relates to new virus forms capable of causing lymphadenopathies which are capable of then developing into acquired immune deficiency syndrome (AIDS). The invention also applies to antigens which may be obtained from these viruses and other viruses having certain properties in common with them. It also concerns antibodies which may be induced against these various antigens. Lastly, the invention relates to using these antigens or antibodies in diagnosing certain AIDS forms and, with respect to some of these AIDS forms, to producing immunizing and vaccinating compositions against these retroviruses such as purified proteins, glycoproteins, recombinant proteins or synthetic peptides.

An article by F. Barre-Sinoussi et al. in Science, Vol 220: pp 868–871 [1983] describes the isolation of the first retrovirus which was known to be responsible for AIDS. European Patent Application 138,667 specifically describes diagnosis of AIDS and pre-AIDS by detection of the presence of antibodies against the virus through the use of certain virus extracts and particularly through the use of some of the viral proteins. This retrovirus is known generally as LAV. Since that time, other similar strains and variations of LAV have been isolated. Illustrative strains include HTLV-III and ARV. The expression Human Immunodeficiency Virus Type I, abbreviated HIV-I, has been coined to cover these designations and the corresponding viral strains. The, the set of viruses which are identical with or close to the initial isolate shall be called herein "LAV type 1" or "LAV-I".

The "LAV" set may be defined as a set of viruses either causing generalized and persistent polyadenopathies, or AIDS, and having in vitro a tropism for T4 cells wherein this retrovirus induces a cytopathogenic effect. These retroviruses have been found to be distinct from the other already known human retroviruses (HTLV-I and HTLV-II).

Even though the LAV virus does vary genetically rather substantially, the diverse strains isolated to date from African, Haitian, European and American patients have in common certain antigenic sites on their main proteins: p25 core protein; gp 110 envelope glycoprotein; and gp 41–43 transmembrane protein. As a result, the prototype strain LAV-I deposited at COLLECTION NATIONALE DES CULTURES DE MICRO-ORGANISMES (CNCM) Institute Pasteur, 28 rue du Docteur Roux, 75724 Paris Cedex 15, France, under No. I-232 may be used as an antigen strain to detect antibodies for all types of afflicted patients regardless of origin. For example, the HTLV-III virus isolated by R. C. Gallo et al. which is presently being used to detect antibodies in blood donors and patients by means of ELISA, immunofluorescence, and "western blot" (or immuno-print) techniques and RIPA (radio immuno-precipitation assay).

SUMMARY OF THE INVENTION

It has now been found in serological research on patients native to Guinea-Bissau and hospitalized in Portugal that some had seronegative or very weakly positive reactions to these tests using an LAV-I lysate, whereas they evinced the clinical and immunological symptoms of AIDS.

Starting with the cultured lymphocytes from one of these patients, a retrovirus was isolated which structure, when examined under electron microscope, and protein contour in SDS electrophoresis gel were generally similar in their properties to those of LAV-I; however, this retrovirus is less related to LAV-I both as regards the antigenic homology of its proteins and the homology of its genetic material than the other, previously identified LAV strains.

Figure 1:
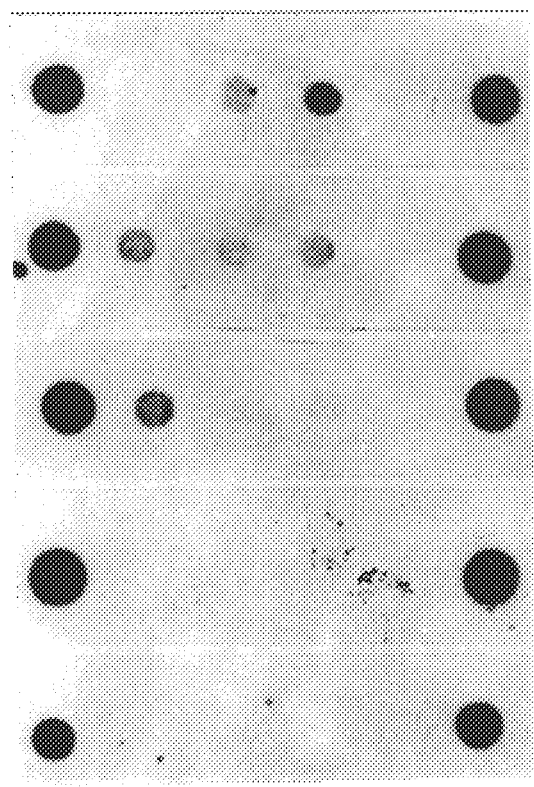
FIG. 1 is a dot-blot hybridization of viral genomic RNA from LAV, STLV-III$_{mac}$, and West African virus isolates with various LAV-I subgenomic DNA probes.
Figure 1:
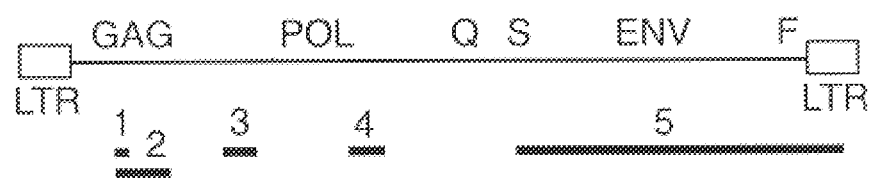

Dot-blot hybridization of viral genomic RNA from LAV, STLV-III$_{mac}$, and West African virus isolates was carried out with various LAV subgenomic DNA probes. Cell culture supernatants (0.5 to 1 ml for each spot) were pelleted for 20 min at 45,000 rpm, the pellet was resuspended in NTE buffer containing 0.1% SDS, and spotted onto nitrocellulose, presoaked in 2×SSC (0.3M NaCl, 0.03M sodium citrate). After baking (2 hours at 80° C.), filters were hybridized with various LAV DNA probes, in non-stringent conditions (30% formamide, 5×SSC, 42° C.), washed in 2×SSC, 0.1% SDS, at 50° C., and autoradiographed for 48 hours at −70° C. with intensifying screens.

Probes 1–4 are single-stranded LAV DNA probes, obtained by, the prime-cut method. Briefly, M13 single-stranded templates carrying LAV-I subgenomic inserts, Wain-Hobson et al., Cell, 1985, Vol 40, p 9–17, were annealed to the 17-mer M13 sequence primer (Biolabs), and the complementary strand was synthesized with Klenow enzyme in TM buffer (Tris 10mM pH 7.5, MgCl$_2$ 10 mM), with DATP, dGTP, dTTP, and alpha-$^{32}$PdCTP (Amersham, 3000 Ci/mMol). DNA was then digested by an appropriate restriction enzyme, heat denatured, and subjected to electrophoresis on a denaturing polyacrylamide gel (6% acrylamide, 8M urea in TBE). The gel was autoradiographed for 5 min, and the probe was cut off and eluted in 300 mM NaCl, 0.1% SDS. Specific activity (AS) of these single stranded probes was estimated to 5×10$^8$–10$^9$ cpm/µg.

In the Figure:

Probe 1: nucleotides 990–1070, probe 2: nucleotides 990–1260, probe 3: nucleotides 2170–2240, probe 4: nucleotides 3370–3640. Probe 5 is a pUC-18 plasmid carrying the EcoRI-SacI fragment (nucleotides 5290–9130) of the LAV clone lambda J19 (31), nick-translated to an AS of approx. 10$^8$ cpm/µg.

Spots A: virus from a LAV-infected CEM cl. 13 culture, Spots B: virus from STLV-III$_{mac}$-infected HUT-78 cells. Spots C and D: virus isolates from patient 2 and 1, respectively. Spots E: negative control from uninfected HUT-78 cells. Spots F: virus from a Zairian patient with AIDS, grown on normal T lymphocytes with TCGF. All spots are made with an amount of virus corresponding to 25,000 cpm of reverse transcriptase activity, except for spots C: 15,000 cpm.

DESCRIPTION OF THE PREFERRED EMBODIMENT

The new retroviruses which are the object of the present patent application and related virus strains are called "LAV type II" or "LAV-II" or "West African AIDS retrovirus". Each isolate is followed by the first three letters of the name of the patient from whom it was isolated. This new retrovirus, hereafter called LAV-II, and retroviruses with antigenically and immunologically equivalent properties, therefore may be used as antigen sources to diagnose infection by this virus and variants that cause, in particular, AIDS, especially in African patients or persons having stayed in Africa.

This virus was isolated from several patients from Guinea-Bissau and Cape Verde Islands, in particular from blood in the form of a heparinized sample of a patient 28 years old from Guinea-Bissau, who is heterosexual, who never had a blood transfusion and who was not a drug addict. Since 1983 he showed significant chronic diarrhea, substantial weight loss (17 kg) and intermittent fever. Recently he has suffered from Candida and Serratia infections, including esophageal candidiasis, typical of AIDS.

He also suffered from anemia, lymphopenia, a ratio of 0.15 of T4 lymphocytes to T8 lymphocytes, and cutaneous anergy. In culture, his lymphocytes remained unresponsive to stimulation by phytohemaglutinin and concanavalin A. The set of these symptoms showed this was a case of ARC (AIDS related complex) of the type caused by the LAV-I virus. Ultimately this was diagnosed as an AIDS case.

The lymphocytes of this patient were cultured and the retrovirus was isolated by the method already described for isolating the LAV-I in the Barre-Sinoussi et al. article, supra, and in the European Patent Application 84 401834/0 138 667. This method shall be briefly summarized here: the lymphocytes are stimulated for 3 days by phytohemaglutinin (PHA). The lymphocytes were cultured in an RPMI-1640 medium to which was added 10% fetal-calf serum, $10^{-5}$M beta mercaptoethanol, interleukin-2 and human alpha anti-interferon serum.

The virus production was followed by detecting its reverse transcriptase activity. In the culture supernatant, the peak viral activity took place between the 14th and the 22nd days, whereupon it declined and ultimately resulted in the death of the cell culture.

The virus was propagated on blood-donor lymphocyte cultures, followed by propagation on continuous cell strains of leukemic origin, such as HUT 78. The virus was characterized as being fairly distinct from LAV-I by examination of its proteins and its nucleic acid. The virus was purified as described in the Barre-Sinoussi et al. article and European Patent Application 84 401834/0138667, supra. It was deposited at the COLLECTION NATIONALE DES CULTURES DE MICRO-ORGANISMES (CNCM) at the Institut Pasteur on 19 Dec. 1985 as CNCM I-502 as LAV-II MIR.

In addition to the first isolate, a second LAV-II isolate has been obtained in a similar manner and deposited at CNCM. This second isolate was deposited on 21 Feb. 1986 as deposit CNCM I-532 as LAV-II ROD. Generally speaking, the invention covers any equivalent virus containing structural proteins with the same immunological properties as those of the LAV-II virus CNCM I-502. Several properties of these constituent proteins are listed below in the form obtained from the test conditions shown hereafter.

(1) Proteins. The virus was metabolically marked with $^{35}$S cysteine or $^{35}$S methionine, the infected cells being incubated in the presence of these radioactive amino acids in a culture medium lacking the corresponding unmarked amino acid for a period of time of 14 to 16 hours. The supernatant was then clarified and i the virus was ultra-centrifuged for 1 hour at 100,000 g in a 20% sucrose gradient. The main virus proteins were separated by electrophoresis in a (12.5%) polyacrylamide gel, and bisacrylamide under denaturing conditions (SDS at 0.15% final concentration). The reference molecular weight is in the form of the following dye markers marketed by BRL Co. for Western blot:

myosine 200 Kd
phosphorylase B 97.4 Kd
BSA 68 Kd
ovalbumin 43 Kd
alpha chymotrypsin 25.7 Kd
beta lactoglobulin 18.4 Kd
lysozyme 14.3 Kd.

For the RIPA assay, molecular weight markers are $^{16}$C-labelled proteins (obtained from Amersham) including:

myosine 200 Kd
beta galactosidase 130 Kd
BSA 69 Kd
phosphorylase B 93 Kd
ovalbumin 46Kd
carbonate anhydrase 30 Kd The proteins are also distinguished following immuno-precipitation (RIPA) or by immuno-print (Western blot) by using the antibodies present in the patient's blood. Their molecular weights as determined by their apparent migration are similar to but different from those of LAV-I: p16, p26 for the two largest inner proteins; gp 130–140 (molecular weight of 130–140 Kd±10%) for the external envelope glycoprotein; and gp 36 (molecular weight 36 Kd±5%) for the transmembrane protein (detected in particular by the Western blot technique). The sera from both patients were examined for the presence of antibodies against LAV, against their own viral isolates, as well as against STLV-III$_{mac}$, isolated from a macaque with simian AIDS, as a STLV-III$_{mac}$-infected HUT-78 culture.

Labelling of infected cell cultures with $^{35}$S cysteine, immunoprecipitation of soluble virus extracts from these cultures followed by SDS-PAGE, and Western blots, were conducted as already described. The serum of both patients failed to react with extracts of $^{35}$S-cysteine labelled LAV. They, however, precipitated weakly and inconstantly a protein of 34 Kd. Sera of both patients were repeatedly negative for anti-LAV-I antibodies in the commercially available ELISA tests.

In virus extracts from the isolate of patient 1, the two sera strongly precipitated a high molecular weight protein (130–140Kd) which can be assumed to be the major envelope glycoprotein, and termed gp 140. Similar results were obtained with extracts from the isolate of patient 2.

Interestingly, the serum from a macaque infected with STLV-III$_{mac}$ also reacted with the same gp 140 in West African AIDS retrovirus extracts, and the sera of the two West-African AIDS patients precipitated a protein with a similar molecular weight in $^{35}$S cysteine-labelled STLV-III virus extracts.

In any of the three types of virus extracts, the sera from both patients, and the macaque's serum, only precipitated very weakly proteins with a molecular weight consistent with gag proteins, as is often the case in some patients with advanced AIDS caused by LAV-I. However, anti-LAV-I reference sera, which never reacted with the gp 140, precipitated a 26K protein in West African retrovirus $^{35}$S cysteine virus extracts. A protein with a molecular weight of 27K was also precipitated by the same sera in STLV-III extracts.

Immunofluorescence experiments, conducted on West African AIDS retrovirus- and STLV-III$_{mac}$-infected HUT-78 cells as well as on LAV-I-infected MOLT cells, have confirmed these results. Sera from West African patients reacted strongly with cells infected with their viral isolate and STLV-III-infected cells, but did not react with LAV-I or LAV-I infected cells. Some anti-LAV sera weakly reacted with both West African AIDS retrovirus- and STLV-III-infected HUT-78 cells, but some others did not react with any of these cells.

Although they display some common antigenic structures, some of the proteins of LAV-I, West African AIDS retrovirus, and STLV-III, differ in molecular weight (MW). See Table 1. The major gag protein of LAV-I has a MW of 25K, whereas it is 27K in 1STLV-III, and seems to be around 26K in the West African AIDS retrovirus. The major envelope glycoprotein observed in RIPA, which corresponds to the outer membrane portion of the whole glycoprotein molecule, is 110 Kd in LAV, but displays a MW of about 140 Kd in both West African isolates LAV-II and STLV-III. The transmembrane portion of this envelope glycoprotein, which is not observed in $^{35}$S cysteine RIPA, but can be identified on Western blots as a broad band, has a MW of approximately 41 Kd in LAV-I, 36 Kd in West African AIDS retrovirus, and 32 Kd in STLV-III. Therefore, it can be assumed that the West African AIDS retrovirus is antigenically related to, but distinct from, both LAV-I and STLV-III. However, the fact that its envelope glycoprotein is precipitated by West African patients' sera and STLV-III infected macaque's serum, suggests that this virus may be more closely related to STLV-III than to LAV-I.

TABLE 1

Relative Molecular Weights of Selected Viral Proteins

|  | LAV-I | STLV-III$_{mac}$ | LAV-II |
| --- | --- | --- | --- |
| External envelope protein | 110/120 | 130–140 | 130–140 |
| Transmembrane protein | 41–43 | 32 | 34–36 |
| Major core protein | 25 | 27–28 | 26 |
| Second largest core protein | 18 | 15 | 16 |

(2) Nucleic acid. The virus RNA deposited on the filter paper following the "spot blot" technique was hybridized under stringent conditions with the DNA probes derived from LAV-1. The "spot blot" technique also is called the "dot blot" (transfer by spots) technique. The term "stringent conditions" refers to those conditions whereby hybridization reactions are carried out by placing the RNA of LAV-II in contact with a selected probe which is radioactively labelled marked with $^{32}$p (or labelled in a different way), namely at 42° C. in the presence of 50% formamide for 18 hours. The membrane on which the hybridization reaction took place was then washed at 65° C. in a buffer containing 0.1% SDS and 0.1×SSC.

"Non-stringent conditions" refers to those wherein the hybridization reactions are carried out by placing the RNA of the LAV-II in contact with a selected probe radioactively labelled with $^{32}$p (or labelled differently), namely at 42° C. in the presence of 30% formamide for 18 hours. The membrane is washed at 45° C. with a buffer containing 0.1% SDS and 2×SSC.

To further determine the relationship between the West African AIDS retrovirus and LAV-I, we have performed dot-blot hybridization experiments with their genomic RNA, obtained from purified viral particles, with various DNA probes derived from LAV-I.

Viral RNA from both LAV-II isolates did not hybridize in stringent conditions with any whole genomic or subgenomic LAV-I DNA probe. This hybridization was repeatedly negative, even though viral particles were purified from several highly infectious culture supernatants with a high reverse transcriptase activity.

In low stringency conditions, viral RNA from both LAV-II isolates was also hybridized with LAV-I DNA subgenomic probes representing different regions of the genome. See FIG. 1. These single-stranded DNA probes were obtained from M13 subclones of the LAV genome, by the prime-cut method. All of these probes, which were complementary of the plus (+) DNA strand, very strongly hybridized with genomic RNA from both LAV-I standard isolate (LAV$_1$) and another LAV-I isolate from a Zairian patient with AIDS. Two probes were obtained from the gag region LAV-I (nucleotides 990–1070 and 990–1260) : both hybridized weakly with the two LAV-II spots, but only one (nucleotides 990–1260) also hybridized with the STLV-III$_{mac}$ spot. See FIG. 1. A probe from the 5' end of the LAV-I pol open reading frame, corresponding to the protease region, hybridized neither with the LAV-II nor with STLV-III spots.

Two additional single stranded probes were obtained from the LAV-I pol region. The first one, from the reverse transcriptase region (nucleotides 2170–2240), hybridized with STLV-III, and only very weakly with the LAV-II. The other one, from the middle of the pol region (nucleotides 3370–3640), failed to hybridize Ilwith LAV-II or STLV-III.

Finally, a nick-translated probe involving the whole LAV-I env gene and the LTR (nucleotides 5290–9130) did not hybridize with either STLV-III or the LAV-II. Additionally, we found no hybridization, with any of the probes used, with spots from supernatant of non-infected cell cultures. See FIG. 1. These data strongly demonstrate that the West African AIDS retroviruses are only distantly related to LAV-I, since their genome seems to cross-hybridize weakly only with domains of the genome of LAV-I which are known to be highly conserved among retroviruses of the same group. Although serological data have revealed a very close relatedness of these isolates with STLV-III$_{mac}$, concerning mainly their envelope antigens, hybridization experiments show that they may differ from this simian retrovirus in some regions such as the gag and even the pol gene.

The LAV-II virus was found to be suitable as a source of antigens to detect antibodies in other African patients. The various LAV-II antigens were recognized by sera from other patients from Bissau-Guinea suffering from ARC and by asymptomatic persons wherein the antibodies immunoprecipitated the LAV-II proteins.

Both LAV-II and LAV-I are cytotoxic with respect to the T4 lymphocytes and are antigenically unrelated to HTLV-I and HTLV-II. In particular, the LAV-II proteins do not cause immunological cross-reactions with the p19 and p24 proteins of HTLV-I and HTLV-II, especially as regards the RIPA (radio-immunoprecipitation assay) techniques.

Generally, this invention relates to any composition containing at least one of the LAV-II proteins, such a composition being suitable for diagnosing the corresponding AIDS variety by implementing the diagnostic method such as described in the above mentioned European patent application. In this respect, the invention specifically covers compounds containing the p16 and 26 internal proteins, or the gp 36 or gp 130–140 glycoproteins. Advantageous compositions are contemplated which contain the entire protein set of LAV-II or several of these proteins and/or glycoproteins. Illustrative are several compositions cited below, which contain:

p26 and gp 36,
p26, gp 36 and gp 130–140,
p16 and p26,
p16, p26 and gp 13 0–140.

Again, the invention relates to each of these proteins when purified in the sense that each of these proteins provides only a single band in the electrophoresis on polyacrylamide gel, particularly under the aforementioned experimental conditions. Any suitable separation and/or purification method for obtaining the protein may be used. Illustrative of such a method is that described by R. C. Montelaro et al. in *J. Virology*, June 1982, pp 1029–1038.

As noted above, these compositions are merely illustrative of the compositions of the present invention. In particular, the invention covers the viral lysates or extracts containing a complete set or any subset of the viral proteins and/or glycoproteins.

However, it must be borne in mind that the expression "compositions containing a protein or glycoprotein of this virus" is not limited to the lysates or extracts of the LAV-II virus. Furthermore, the invention concerns compositions associating proteins and/or glycoproteins of LAV-II with proteins and/or glycoproteins of LAV-I. Such compositions, when used for diagnostic purposes, thereby allow AIDS diagnosis or diagnosis of its associated symptoms covering a broader spectrum of the causative etiological agents. However, the use of compositions containing only proteins and/or glycoproteins of LAV-II for diagnosis does not degrade its usefulness for more selective diagnosis of a retrovirus category that might be responsible for the particular ailment. Such compositions (purified proteins, recombinant proteins obtained by the expression in prokaryotic or eukaryotic cells of the LAV-II genome or synthetic peptides deduced from the sequence of the genome) may be used for purposes of vaccination by inducing the synthesis of a protective immune response after administration to the host. Additionally, for therapeutic purposes, peptides could be developed which would be capable of inhibiting the binding of LAV-II to susceptible cells and thus prevent the spread of infection. An immunizing composition can comprise an envelope glycoprotein of LAV-II in conjunction with a pharmaceutically acceptable vehicle. A dose of the immunizing composition can contain the antigen in an amount sufficient for administration of 10 to 500 micrograms antigen per kilogram of body weight, in particular 10 to 50 micrograms antigen per kilogram of body weight.

In general, the invention covers all compositions of this type containing a protein, a glycoprotein or polypeptide having immunological properties equivalent to those of LAV-II. Two proteins are said to be "equivalent" within the scope of this discussion when they are capable of being recognized by the same antibodies. The products expressed by corresponding sequences of the coding DNA's of corresponding polypeptide sequences are thus among the equivalent polypeptides, proteins or glycoproteins.

Another aspect of the invention are the DNA's or fragments, of DNA's obtained from the RNA or from cDNA's derived from the RNA of the LAV-II retrovirus. The invention concerns in particular all equivalent DNAs, especially any DNA evincing at least 70% sequential homology with the LAV-II-derived DNA. In general, the scope of the invention covers any equivalent DNA (or RNA) capable of hybridization with the LAV-II RNA or LAV-II-derived DNA by the spot blot technique in the conditions as defined above.

Furthermore, the invention relates to the sera which might be produced from animals by inoculating them with LAV-II with compositions as defined above. In particular, an aspect of the invention includes polyclonal antibodies which are specifically aimed at each of the virus proteins or glycoproteins. Moreover, another aspect of the invention are monoclonal antibodies which may be produced by conventional techniques and which are directed more specifically at the various LAV-II proteins.

These polyclonal or monoclonal antibodies may be used in a variety of applications. Among these is the neutralization of corresponding proteins, including inhibition of the infectiousness of the entire virus. They may also be used to detect viral antigens in biological preparations or in purifying corresponding proteins and/or glycoproteins, for example when used in affinity chromatography columns.

It is implied herein that as a rule the available literature relating to LAV-I, and the virus denoted HTLV-III, must be considered part of the present invention when the techniques described in this literature apply in similar conditions to isolating the LAV-II virus or equivalent viruses or to obtaining the various constituents from these viruses, in particular proteins, glycoproteins, polypeptides and nucleic acids. Again, one may resort to the teachings of this technical literature to use the various constituents in diagnostic operations for the corresponding forms of AIDS or PGL (persistent generalized lymphadenopathy--also known as LAS).

Another aspect of the invention is any equivalent virus exhibiting the intrinsic LAV-II immunological characteristics. In general, the invention therefore relates to any virus which, beyond the properties shown by either or both of the LAV-II strains deposited at CNCM, also has the following characteristics.

The preferred targets of the LAV-II retrovirus are the Leu 3 cells (or T4 lymphocytes). LAV-II has a reverse transcriptase activity requiring the presence of $Mg^{2+}$ ions and shows a strong activity toward poly(adenylate-oligodeoxythymidylate) (poly[A]oligo-[dT] $_{12-18}$). Its specific gravity is 1.16 in a sucrose gradient. Its mean diameter is 140 nm and its core has a mean diameter of 41 nm. The lysates of this virus contain a p26 protein which does not immunologically crossreact with the p24 protein of the HTLV-I virus or the HTLV-II virus. It contains a p16 protein which is not immunologically recognized by antibodies against the p19 protein of HTLV-I or HTLV-II. It is cytotoxic to the human T4 lymphocytes. It can be cultivated in the permanent HUT-78 cell line, CEM and MOLT cells lines and other cell lines exhibiting the T4 protein.

Another aspect of the invention is a production method for the LAV-II virus in permanent cell strains derived from T4 lymphocytes, for instance the HUT 78 cell type (strain registered at CNCM as I-519 on 6 Feb. 1986), where this method consists of cultivating these strains previously infected with the LAV-II virus and in recovering the quantities of virus which are released into the culture medium. The prior infection may be carried out as follows:

The HUT 78 cells ($10^6$/ml) are placed in co-cultures with infected normal human lymphocytes ($10^6$/ml) in RPMI 1640 medium with 10% fetal calf serum. After 15 to 21 days, a cytopathogenic effect is observed in the HUT 78 cells, characterized by the appearance of multi-nucleated giant cells. At the same time reverse transcriptase was detected in the culture supernatant.

A more particular aspect of the present invention is the development of an in vitro diagnostic procedure for AIDS which comprises placing a serum or another biological medium from a patient to be diagnosed in contact with at least one of the proteins or glycoproteins of LAV-II, or with a virus lysate or extract, and then detecting the immunological reaction. Preferred implementing methods include for example the ELISA and immunoenzymatic reactions or immunofluorescent materials. The assays may be direct or indirect immunofluorescence measurements or direct or indirect immunoenzymatic dosages.

Therefore, the present invention also applies to labelled virus extracts regardless of whether the labelling is enzymatic, fluorescent, radioactive, etc.

Such assays illustratively include:

depositing specific extract quantities or quantities of the proteins of the present invention in the wells of a titration microplate;

introducing increasingly higher dilutions of the serum to be diagnosed into these wells;

incubating the microplate;

carefully washing the microplate with a suitable buffer;

introducing antibodies which are specifically labelled with human immunoglobulins into the wells of the microplate, the labelling being carried out by an enzyme selected from those capable of hydrolyzing a substrate in such a manner that this substrate thereupon alters its radiation-absorptivity at least within a specific band of wavelengths; and detecting, preferably in comparative manner with respect to a control, the amount of substrate hydrolysis both with respect to measuring potential danger and any actual presence of the ailment.

Another aspect of the present invention are kits for the above diagnostic procedure. These kits include:

an extract or a more purified fraction of the above described virus types, where this extract or fraction is labelled, for example radioactively, enzymatically or by imunofluorescence;

human anti-immunoglobulins or a protein A (advantageously fixed on a water-insoluble support such as agarose spheres);

an extract of lymphocytes obtained from a healthly person;

buffers, and where called for, substrates to visualize the labels.

From what already was stated above and is obvious per se, the invention is not limited in any way to the applicable modes and its implementations which were discussed more specifically; on the contrary it includes all variations, in particular those still being cited in the claims below and which thereby must be considered integrated or to be integratable into the present specification.

Be it noted furthermore that in the numerical data below, the notations "p" and/or "gp" denote the approximate molecular weights of the proteins and/or glycoproteins being discussed but divided by 1,000. Illustratively, "gp 36" denotes a molecular weight of approximately 36,000. Be it also noted that, for the same experimental conditions as those prevailing in the determination of the molecular weights of the LAV-II proteins, the STLV-III virus described by Letvin et al. (Science 1985, vol. 230, p 71), has a transmembrane glycoprotein of 32 Kd whereas the LAV-II transamembrane protein has a molecular weight of 36 Kd.

What is claimed is:

1. A purified antibody which binds specifically to gp36 of human immunodeficiency virus type 2 (HIV-2).

2. The antibody according to claim 1, wherein said antibody is a monoclonal antibody.

3. A purified antibody which binds specifically to p16 of human immunodeficiency virus type 2 (HIV-2).

4. The antibody according to claim 3, wherein said antibody is a monoclonal antibody.

5. A purified antibody which binds specifically to p26 of human immunodeficiency virus type 2 (HIV-2).

6. The antibody according to claim 5, wherein said antibody is a monoclonal antibody.

7. The antibody according to any one of claims 1–6, wherein the antibody is labeled with a label selected from the group consisting of a radioactive label, an enzymatic label, a fluorescent label, a chemiluminescent label, and a chromophore label.

* * * * *